(12) United States Patent
Monzen et al.

(10) Patent No.: US 6,180,801 B1
(45) Date of Patent: Jan. 30, 2001

(54) METHOD FOR MANUFACTURING 3-ISOCHROMANONE

(75) Inventors: Hiroyuki Monzen; Hideo Miyata; Kimitaka Ooshiro; Kohei Morikawa, all of Kawasaki (JP)

(73) Assignee: Showa Denko Kabushiki Kaisha, Tokyo (JP)

(*) Notice: Under 35 U.S.C. 154(b), the term of this patent shall be extended for 0 days.

(21) Appl. No.: 09/277,941

(22) Filed: Mar. 29, 1999

Related U.S. Application Data

(60) Provisional application No. 60/083,103, filed on Apr. 28, 1998.

(30) Foreign Application Priority Data

Mar. 30, 1998 (JP) .................................. 10-084499

(51) Int. Cl.$^7$ ................................. C07D 311/02
(52) U.S. Cl. .............................................. 549/283
(58) Field of Search ................................... 549/283

(56) References Cited

PUBLICATIONS

S.P. Khanapure and E.R. Biehl, "Preparation of 4–Alkyl and 4–Aryl Derivatives of 6–(Acetoxymethyl)isochroman–3–one", *J. Org. Chem.*, 1987, 52:1333–37.

Kanapure et al, Chemical Abstract vol. 112 NO. 118597 "Prep. of novel 4–substituted 6–methoxy–6,7–dimethoxy & 6,7 methylenedioxy isochroman–3–ones" 1990.*

* cited by examiner

*Primary Examiner*—John Kight
*Assistant Examiner*—Raymond Covington
(74) *Attorney, Agent, or Firm*—Sughrue, Mion, Zinn, Macpeak & Seas, PLLC

(57) ABSTRACT

The present invention intends to provide a method for producing 3-isochromanones represented by formula (II) useful as a synthetic starting material of medicals or agricultural chemicals and the cyano compound represented by formula (I) by an industrially advantageous method in a high yield.

Disclosed herein is a method for manufacturing a 3-isochromanone represented by the following formula (II):

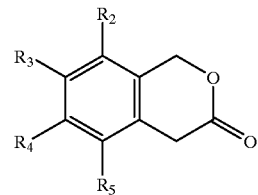

(II)

(wherein $R_2$, $R_3$, $R_4$ and $R_5$ each independently represents a hydrogen atom, a halogen atom, an alkyl group or an alkoxy group), said method is characterized by comprising the steps of:
hydrolyzing a cyano compound represented by formula (I):

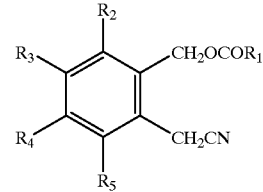

(I)

(wherein $R_1$ represents a hydrogen atom, an alkyl group or an aryl group, and $R_2$, $R_3$, $R_4$ and $R_5$ have the same meanings as defined above) and subjecting the hydrolyzate to intra-molecular cyclization.

21 Claims, No Drawings

METHOD FOR MANUFACTURING 3-ISOCHROMANONE

CROSS REFERENCE TO RELATED APPLICATION

This application is an application fired under 35 U.S.C §111(a) claiming benefit pursuant to 35 U.S.C §119(e)(1) of the filing date of the Provisional Application Ser. No. 60/083,103, filed Apr. 28, 1998, pursuant to 35 U.S.C. §111(b).

TECHNICAL FIELD OF THE INVENTION

The present invention relates to a method for manufacturing a 3-isochromanone useful as an intermediate of medicals or agricultural chemicals, and a method for manufacturing a cyano compound which can be used as a starting material in the manufacturing method of 3-isochromanones.

BACKGROUND OF THE INVENTION

For manufacturing a 3-isochromanone represented by the later described formula (II), some different methods have been proposed. For example, JP-A-9-67364 (the term "JP-A" as used herein means an "unexamined published Japanese patent application") discloses a method of reacting α,α'-dihalogeno-o-xylene with carbon monoxide and water in the presence of a hydrogen halogenide scavenger and a-complex catalyst containing a metal such as palladium. Furthermore, A. Cowell et al have reported that 3-isochromanone is synthesized by reacting o-bromomethylbenzyl alcohol with carbon monoxide in the presence of a palladium complex catalyst (JACS., 102, 4191 (1980)).

Also, in some methods hitherto proposed, 3-isochromanone is synthesized by the Baeyer-Villiger oxidation reaction using 2-indanone as a starting material. More specifically, A. Chatterjee et al, P. Cottet et al and C. Kocch et al disclose a method of synthesizing 3-isochromanone by reacting 2-isodandne with a metachloroperbenzoic acid (see, Synthesis, 818 (1981), Synthesis, 497 (1987), Synthetic Communication, 19, 829 (1989)). F. G. Mann et al disclose a method of synthesizing 3-isochromanone by reacting α-methoxy-α'-cyano-o-xylene in an aqueous sulfuric acid solution (see, J. Chem. Soc., 2819 (1954)). Furthermore, U. Azzena et al disclose a method of synthesizing 3-isochromanone by ring-opening phthalan with a metal lithium, reacting it with carbon dioxide and hydrolyzing the reaction product (see, Tetrahedron Lett., 36, 8123 (1995)).

However, these methods are not an industrially useful method because the starting materials are difficult to be synthesized and prevented from the industrial use for general purposes, an expensive reagent or catalyst is necessary to be used or the yield is low.

OBJECT OF THE INVENTION

The object of the present invention is to manufacture a 3-isochromanone represented by formula (II) by an industrially advantageous method in a high yield.

SUMMARY OF THE INVENTION

The present invention relates to a method for manufacturing a 3-isochromanone represented by formula (II):

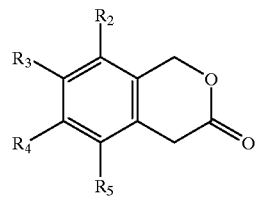

(II)

(wherein $R_2$, $R_3$, $R_4$ and $R_5$ each independently represents a hydrogen atom, a halogen atom, an alkyl group or an alkoxy group (hereinafter, unless otherwise indicated, $R_2$ to $R_5$ have the same meanings)), said method comprising hydrolyzing a cyano compound represented by formula (I):

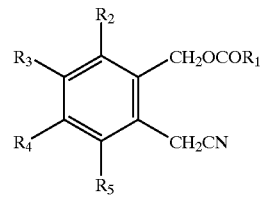

(I)

(wherein $R_1$ represents a hydrogen atom, an alkyl group or an aryl group (hereinafter, unless otherwise indicated, $R_1$ has the same meaning)) and subjecting the hydrolyzate to intramolecular cyclization.

In the present invention, the hydrolysis is preferably performed in the presence of an acid or an alkali and the intramolecular cyclization is preferably performed in the presence of an acid;

The hydrolysis is preferred to be performed in the presence of an acid.

Moreover, in the above formula (I), $R_1$ is preferably a hydrogen atom or an alkyl group having from 1 to 9 carbon atoms, and particularly a methyl group, an ethyl group or a 3-n-heptyl group. Further, in the formula (I), $R_2$, $R_3$, $R_4$ and $R_5$ each is preferably a hydrogen atom.

Further, in the present invention, it is preferred that the 3-isochromanone is separated by distillation from the reaction mixture of the intramolecular cyclization.

Still further, the present invention relates to a method for manufacturing a cyano compound represented by formula (I), comprising reacting a monoester compound represented by formula (III):

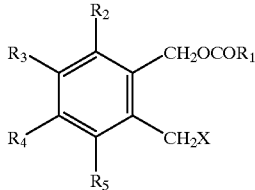

(III)

(X represents a halogen atom (hereinafter, unless otherwise indicated, X has the same meaning)) with a metal cyanide.

In the method for manufacturing a 3-isochromanone according to the present invention, it is particularly preferable that the cyano compound is manufactured by the method described above.

In the present invention, the monoester compound represented by formula (III) is preferably manufactured by reacting an α,α'-dihalogeno-o-xylene compound represented by formula (IV):

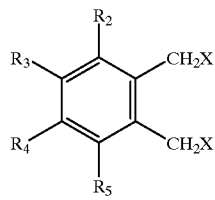

with an alkali metal salt or alkaline earth metal salt (hereinafter, collectively called a "carboxylic acid alkali salt") of a carboxylic acid represented by $R_1COOH$ (wherein $R_1$ represents a hydrogen atom, an alkyl group or an aryl group).

In the above, it is preferred that the α,α-dihalogeno-o-xylene compound is reacted in an amount of 2 equivalent or more to the carboxylic acid alkali salt.

Particularly, it is preferable that after the reaction of the α,α'-dihalogeno-o-xylene compound with the carboxylic acid alkali salt, the unreacted α,α'-dihalogeno-o-xylene compound is separated and recovered by distillation from the reaction mixture.

Still more, in the above method, it is preferred that an aprotic polar solvent is added to the reaction system of the α,α'-dihalogeno-o-xylene compound with the carboxylic acid alkali salt.

DETAILED DESCRIPTION OF THE INVENTION

The present invention is described in detail below.
Manufacturing Method of 3-Isochromanones (II)
The cyano compound (I) is hydrolyzed with an alkali such as sodium hydroxide according to reaction scheme (a):

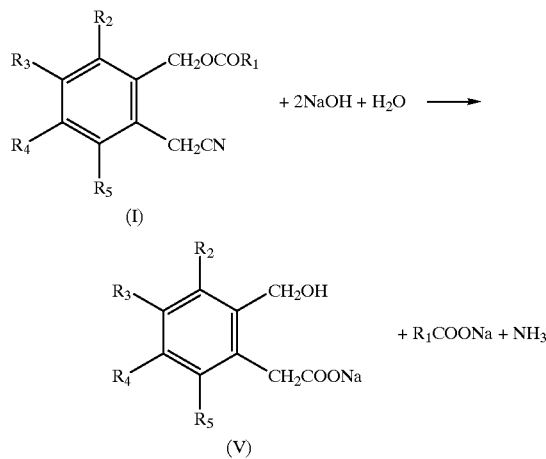

to synthesize a 2-(hydroxymethyl)phenylacetic acid compound (V). The 2-(hydroxymethyl)phenyl acetic acid compound produced is subjected to intramolecular cyclization in the presence of an acid such as hydrochloric acid according to reaction scheme (b):

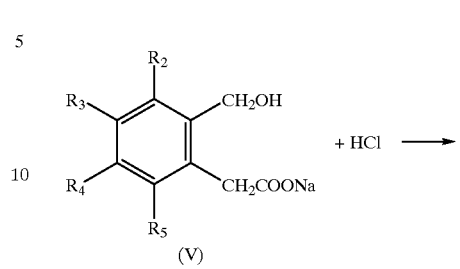

to synthesize a 3-isochromanone (II). The intermediate product 2-(hydroxymethyl)phenylacetic acid compound (V) may be isolated, optionally purified and then used for the manufacturing of a 3-isochromanone. However, an acid such as hydrochloric acid may be added to the reaction mixture as it is after the hydrolysis to perform intramolecular cyclization according to reaction scheme (c):

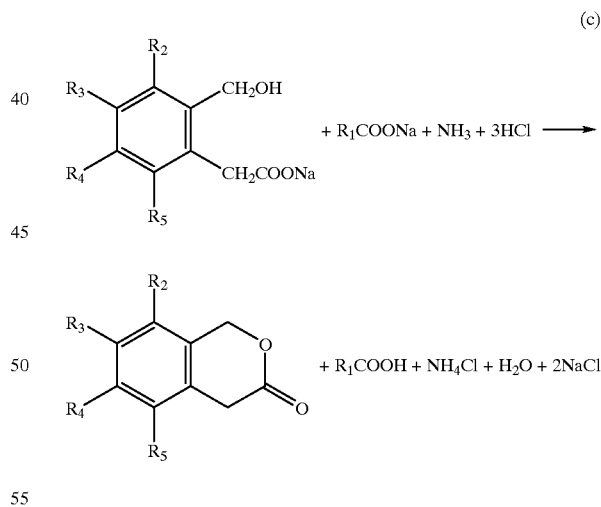

Furthermore, the cyano compound (I) may be subjected to hydrolysis and intramolecular cyclization at the same time in the presence of an acid such as hydrochloric acid according to reaction scheme (d):

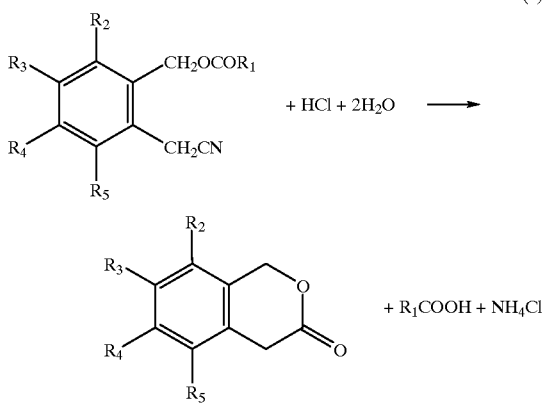

to synthesize a 3-isochromaonone (II).

The cyano compound (I) is represented by formula (I) and in the formula, $R_1$ represents a hydrogen atom, an alkyl group or an aryl group. The alkyl group may be either a linear or branched alkyl group. The alkyl group may also be substituted by a group substantially inert to the reaction, such as an aryl group or a halogen atom. The alkyl group is specifically an alkyl group having from 1 to 9 carbon atoms and specific examples thereof include a methyl group, an ethyl group, a n-propyl group, a heptyl group and a 3-n-heptyl group. Examples of the aryl group include a phenyl group and a naphthyl group. The aryl group also includes an aryl group having a substituent such as an alkyl group, an alkoxy group, a carboxyl group or a hydroxyl group. Among them, $R_1$ is preferably hydrogen atom or an alkyl group having 1 to 9 carbon atoms, particularly, methyl, ethyl or 3-n-heptyl. $R_2$, $R_3$, $R_4$ and $R_5$ each independently represents a hydrogen atom, a halogen atom, an alkyl group or an alkoxy group. Examples of the halogen atom include a fluorine atom, a chlorine atom and a bromine atom. The alkyl group may be either a linear or branched alkyl group. The alkoxy group may be either a linear or branched alkoxy group. Preferably, $R_2$, $R_3$, $R_4$ and $R_5$ each is a hydrogen atom. Specific preferred examples of the cyano compound (I) include [2-(cyanomethyl)phenyl]methyl acetate, [2-(cyanomethyl)phenyl]methyl propionate and [2-(cyanomethyl)phenyl]methyl 2-ethylhexanoate.

The hydrolysis is preferably performed in the presence of an acid or alkali.

In the case where the hydrolysis is performed in the presence of an alkali, the alkali used is sodium hydroxide, potassium hydroxide, calcium hydroxide, magnesium hydroxide or the like, preferably sodium hydroxide or potassium hydroxide. The alkali used may be supplied either in the form of a solid or an aqueous solution. In the hydrolysis using an alkali, water is necessary to be added in an equimolar or greater amount to the cyano compound. The hydrolysis using an alkali may be performed without using a solvent but may also be performed using an alcohol-base solvent such as methanol or ethanol. A water-insoluble organic solvent such as benzene, toluene or xylene may also be used. The reaction temperature is not particularly limited, however, the hydrolysis is preferably performed at a temperature of from room temperature to 150° C.

In the case where the hydrolysis is performed in the presence of an acid, the acid used is hydrochloric acid, sulfuric acid, nitric acid, phosphoric acid, hydrogen bromide or the like, preferably hydrochloric acid or sulfuric acid. Water may be sufficient if it is used in an equimolar or greater amount and water may also be used as a solvent for the acid. Furthermore, an alcohol-base solvent such as methanol or ethanol, a hydrophilic organic solvent such as N,N-dimethylformamide, dimethylsulfoxide or dioxane, or the like may be used. A water-insoluble organic solvent such as benzene, toluene or xylene may also be used. The reaction temperature is preferably from room temperature to the reflux temperature of the solvent.

The intramolecular cyclization is preferably performed in the presence of an acid. In this case, the acid used is hydrochloric acid, sulfuric acid, nitric acid, phosphoric acid, hydrogen bromide or the like, preferably hydrochloric acid or sulfuric acid. The acid may be used in the form of an aqueous solution but hydrogen chloride or hydrogen bromide may be supplied to the reaction vessel as a gas. The intermediate product 2-(hydroxymethyl)phenylacetic acid compound (V) may also be subjected as it is to intramolecular cyclization without passing through isolation and purification. The intramolecular cyclization may be performed without using a solvent but may also be performed using water, an alcohol-base solvent such as methanol or ethanol, a hydrophilic organic solvent such as N,N-dimethylformamide, dimethylsulfoxide or dioxane, or the like. Furthermore, a water-insoluble organic solvent such as benzene, toluene or xylene may be used. The reaction temperature is not particularly limited, however, the intramolecular cyclization is preferably performed at a temperature of from room temperature to 150° C.

In the case where hydrolysis and intramolecular cyclization are simultaneously performed in the presence of an acid, the acid used is hydrochloric acid, sulfuric acid, nitric acid, hydrogen bromide or the like, preferably sulfuric acid or hydrochloric acid. The acid may be used in the form of an aqueous solution but hydrogen chloride or hydrogen bromide may be supplied to the reaction vessel as a gas. The amount of water added may be sufficient if it is 2 equivalent or greater to the cyano compound. The reaction may be performed without using a solvent but may also be performed using an alcohol-base solvent such as methanol or ethanol, a hydrophilic organic solvent such as N,N-dimethylformamide, dimethylsulfoxide or dioxane, or the like. A water-insoluble organic solvent such as benzene, toluene or xylene may also be used. The reaction temperature is not particularly limited, however, the reaction is preferably performed at a temperature of from room temperature to 150° C.

The 3-isochromanone (II) may be purified by an operation such as distillation, extraction or recrystallization. Distillation is a particularly effective means. The 3-isochromanone (II) and carboxylic acid produced by the hydrolysis and intramolecular cyclization are separated by distillation to produce a high-purity 3-isochromanone (II) and the carboxylic acid recovered can be used again as a starting material. Accordingly, the production process is industrially highly efficient.

Production Process of Cyano Compound (I)

The cyano compound (I) can be produced by the reaction of a monoester compound (III) with a metal cyanide such as sodium cyanide according to reaction scheme (e):

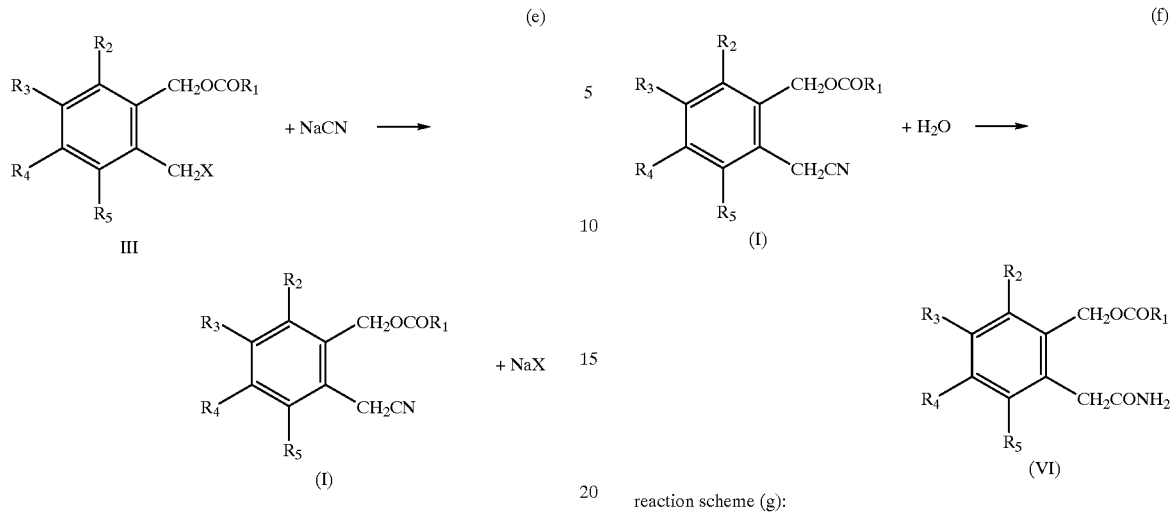

(e)

(I)

The monoester compound (III) is a compound represented by formula (III) wherein $R_1$ represents a hydrogen atom, an alkyl group or an aryl group. The alkyl group may be either a linear or branched alkyl group. The alkyl group may be substituted by an aryl group, a halogen atom or the like. The alkyl group is preferably an alkyl group having from 1 to 9 carbon atoms, more preferably a methyl group, an ethyl group, a n-propyl group, a n-heptyl group or a 3-n-heptyl group. The aryl group is, for example, a phenyl group or a naphthyl group. The aryl group may have a substituent such as an alkyl group, an alkoxy group, a carboxyl group or a hydroxyl group. $R_2$, $R_3$, $R_4$ and $R_5$ each independently represents a hydrogen atom, a halogen atom, an alkyl group or an alkoxy group. The halogen atom includes a fluorine atom, a chlorine atom and a bromine atom. The alkyl group may be either a linear or branched alkyl group. The alkoxy group may be either a linear or branched alkoxy group. X represents a halogen atom and specific examples thereof include a fluorine atom, a chlorine atom, a bromine atom and an iodine atom. A chlorine atom is industrially preferred. Specific preferred examples of the monoester compound (III) include [2-(chloromethyl)phenyl]methyl acetate, [2-chloromethyl)-phenyl]methyl propionate and [2-(chloromethyl)phenyl]methyl 2-ethylhexanoate.

Examples of the metal cyanide used for the cyanization include sodium cyanide and potassium cyanide.

The metal cyanide may be supplied either in the form of a solid or an aqueous solution. The cyanization may be performed without using a solvent but may also be performed using water, an alcohol-base solvent such as methanol or ethanol, a hydrophilic organic solvent such as N,N-dimethylformamide, dimethylsulfoxide or dioxane, or the like. Furthermore, a water-insoluble organic solvent such as benzene, toluene or xylene may be used. The reaction temperature is not particularly limited, however, the cyanization is preferably performed at a temperature of from room temperature to 150° C.

Depending on the reaction conditions, the cyano compound (I) may be partially hydrolyzed according to reaction scheme (f):

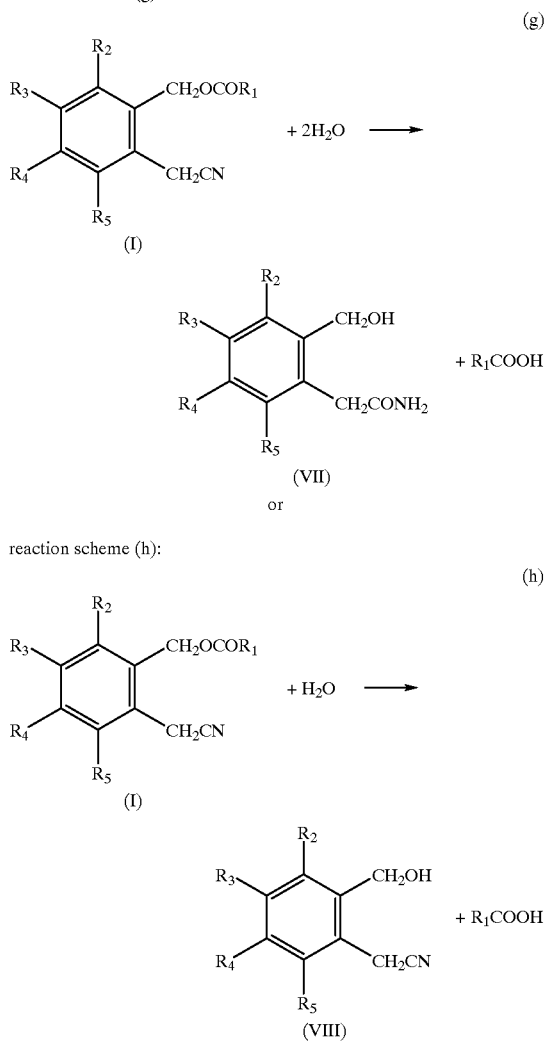

to produce an amide (VI) or (VII) or a [2-(hyroxymethyl)-phenyl]acetonitrile (VIII). These products all can be used as an effective precursor component of the 3-isochromanone (II).

The cyano compound (I) may be used after purifying it by the operation such as distillation, extraction or recrystallization, however, in the case where a large amount of an amide (VI) or (VII) or a [2-(hydroxy-methyl)phenyl] acetonitrile (VIII) which all can be used as a precursor of the 3-isochromanone is produced, use of the compound as it is in the production of 3-isochromanones is also effective.

Production Process of monoester Compound (III) and Manufacturing Method of 3-Isochromanones (II) Including the Process The monoester compound (III) can be produced by reacting an α,α'-dihalogeno-o-xylene compound (IV) with a carboxylic acid alkali salt such as sodium carboxylate according to reaction scheme (i):

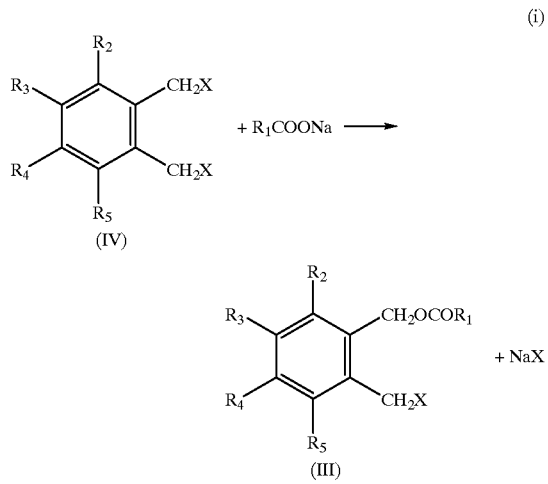

In the α,α'-dihalogeno-o-xylene compound (IV), $R_2$, $R_3$, $R_4$ and $R_5$ each represents a hydrogen atom, a halogen atom, an alkyl group or an alkoxy group. Examples of the halogen atom include a fluorine atom, a chlorine atom or a bromine atom. The alkyl group may be either a linear or branched alkyl group. The halogen atom represented by X is a fluorine atom, a chlorine atom, a bromine atom or an iodine atom. The α,α'-dihalogeno-o-xylene compound (IV) is preferably an α,α'-dichloro-o-xylene.

Examples of the carboxylic acid alkali salt include alkali metal salts and alkaline earth metal salts of a linear or branched aliphatic carboxylic acid. The carboxylic acid alkali salt is preferably an alkali metal salt or alkaline earth metal salt of an aliphatic carboxylic acid having from 1 to 10 carbon atoms, more preferably an alkali metal salt or alkaline earth metal salt of an acetic acid, a propionic acid or a 2-ethylhexanoic acid. An alkali metal salt or alkaline earth metal salt of an aromatic carboxylic acid may also be used and examples thereof include alkali metal salts and alkaline earth metal salts of a benzoic acid or terephthalic acid. Preferred examples of the alkali metal element or alkaline earth metal element in the carboxylic acid alkali metal salt or alkaline earth metal salt include sodium, potassium, calcium and magnesium. Sodium acetate, sodium propionate and sodium 2-ethylhexanoate are preferred because these are easy to be produced starting from a carboxylic acid which is industrially used for general purposes.

The carboxylic acid alkali salt is produced by the reaction of a carboxylic acid with a hydroxide of an alkali metal or a hydroxide of an alkaline earth metal. In the case when an alkali metal hydroxide or alkaline earth metal hydroxide is contained in the alkali metal salt or alkaline earth metal salt of the carboxylic acid, it lowers the yield of esterification in reaction scheme (i). In order to reduce the content of the alkali metal hydroxide or alkaline earth metal hydroxide, for example, the alkali metal salt or alkaline earth metal salt of the carboxylic acid may be produced under the condition such that the amount of the carboxylic acid used is one equivalent or more to the alkali metal hydroxide or alkaline earth metal hydroxide. It is an effective means to thoroughly dry the carboxylic acid alkali metal salt or alkaline earth metal salt produced to thereby reduce the water content. The carboxylic acid alkali metal salt or alkaline earth metal salt produced by the reaction of a carboxylic acid with an alkali metal hydroxide or alkaline earth metal hydroxide may be sometimes in the gel state depending on the kind of the carboxylic acid used. This often occurs when a carboxylic acid having a large molecular weight or a linear carboxylic acid is used. In such a case, there arises difficulty in the handing during the process and water can be hardly removed by drying.

The carboxylic acid alkali salt may be supplied to the reaction vessel either in the form of a solid as it is or in the form of a solution after dissolving it in an aprotic polar solvent such as N,N-dimethylformamide, dimethylsulfoxide or dioxane.

The esterification is preferably performed under the condition such that the ratio of α,α'-dihalogeno-o-xylene compound (IV) added is one equivalent or more to the alkali metal salt or alkaline earth metal salt of the carboxylic acid. The term "equivalent" as used herein means an amount determined by the stoichiometry, for example, in reaction scheme (i). The added ratio is more preferably 2 equivalent or more, so that production of a diester compound resulting from the reaction of α,α'-dihalogeno-o-xylene compound (IV) with 2 molecules of the carboxylic acid can be reduced.

The esterification may be performed without using a solvent, however, by adding an aprotic polar solvent such as N,N-dimethylformamide, dimethylsulfoxide or dioxane, the reaction rate can be effectively improved.

The reaction temperature is not particularly limited, however, the esterification is preferably performed at a temperature of from room temperature to 150° C.

The monoester compound (III) may be used after separating the unreacted α,α'-dihalogeno-o-xylene compound (IV) by distillation. The monoester compound may be purified before use, however, the compound after removal of α,α'-dihalogeno-o-xylene compound (IV) by distillation may be used as it is. The α,α'-dihalogeno-o-xylene compound (IV) recovered can be used again as a starting material and therefore, the production process is industrially highly efficient.

EXAMPLES

The present invention is described in greater detail below by referring to the Examples, however, the present invention is of course not limited to these examples.

Example 1

To a glass-made three-necked flask (volume: 100 ml) with a condenser, 6.2 g of [2-(cyanomethyl)phenyl]methyl acetate (purity: 73%, [2-(hydroxymethyl)phenyl]acetonitrile content: 13%) and 10.0 g of concentrated hydrochloric acid (36 wt % HCl) were added, and the mixture was stirred at 100° C. for 2.5 hours. After the reaction mixture was allowed to cool, 80 ml of toluene and 20 ml of saturated brine were added thereto and the organic layer was separated by the two layer separation. The organic layer was again washed with 20 ml of saturated brine and then the organic layer was recovered. The toluene was distilled off in an evaporator to obtain 7.5 g of an oily component. The oily component had a 3-isochromanone content of 6.1 g (41 mmol). The yield of 3-isochromanone was 124 mol % based on the [2-(cyanomethyl)phenyl]methyl acetate (33 mmol) in the raw materials. The yield exceeded 100% because the product contained [2-(hydroxymethyl)phenyl]acetonitrile or the like which is a precursor of 3-isochromanone, present in the raw materials.

Example 2

To a glass-made three-necked flask (volume: 100 ml) with a condenser, 10.0 g of [2-(cyanomethyl)phenyl]methyl acetate (purity: 86%, [2-(hydroxymethyl)phenyl]acetonitrile content: 8%), 10.0 g of toluene and 13.4 g of a 50% aqueous sulfuric acid solution were added, and the mixture was stirred at 74° C. for 4 hours. Further, 13.4 g of a 50% aqueous sulfuric acid solution was added and the mixture was heated at 74° C. for one hour. Thereafter, the reaction mixture was heated to 93° C., stirred for one hour, and after raising the temperature to 100° C., continuously heated for 3 hours. Then, the reaction mixture was allowed to cool, toluene and saturated brine were added thereto and 47.1 g of the organic layer was separated by the two layer separation. The organic layer was analyzed by the gas chromatography, as a result, the 3-isochromanone content was 6.53 g (44 mmol). The yield of 3-isochromanone was quantitative, 102 mol% based on the [2-(cyanomethyl)phenyl]methyl acetate (43 mmol) in the raw materials.

Example 3

To a glass-made three-necked flask (volume: 100 ml) with a condenser, 50.0 g of [2-(chloromethyl)phenyl]methyl acetate (purity: 89%) and 50.0 g of dimethyl sulfoxide were added, and the mixture was heated to 80° C. Thereto, 50.0 g of a 34 wt % aqueous sodium cyanide solution was added dropwise while stirring over one hour. After completion of the dropwise addition, the mixed solution was continuously stirred for one hour while keeping the temperature at 80° C. The reaction mixture obtained was analyzed by the gas chromatography. As a result, the amount of [2-(cyanomethyl)phenyl]methyl acetate produced was 34.0 g (180 mmol) and the yield was 80 mol % based on [2-(chloromethyl)-phenyl]methyl acetate. Also, it was verified that 3.6 g (24 mmol) of [2-(hydroxymethyl)phenyl]acetonitrile which is a precursor of 3-isochromanone was produced.

Reference Example 1

To a glass-made three-necked flask (volume: 100 ml) with a condenser, 30.0 g (171 mmol) of α,α'-dichloro-o-xylene, 3.0 g of N,N-dimethylformamide and 8.3 g (86 mmol) of sodium propionate were added. After the mixture was heated and stirred at 110° C. for 2.5 hours, the reaction mixture was analyzed by the gas chromatography. As a result, the conversion of α,α'-dichloro-o-xylene was 42% and the yield of [2-(chloromethyl)phenyl]methyl propionate (based on sodium propionate) was 74%.

Reference Example 2

To a glass-made three-necked flask (volume: 500 ml) with a condenser, 66.5 g (380 mmol) of α,α'-dichloro-o-xylene, 66.5 g of N,N-dimethylformamide and 63.2 g (380 mmol) of sodium 2-ethylhexanoate were added. After the mixture was heated and stirred at 120° C. for one hour, the reaction mixture was analyzed by the gas chromatography. The conversion of α,α'-dichloro-o-xylene, the yield of [2-(chloromethyl)phenyl]methyl 2-ethylhexanoate (based on sodium 2-ethylhexanoate), and the molar ratio of the [2-(chloromethyl)phenyl]methyl 2-ethylhexanoate produced to the diester compound as a by-product are shown in Table 1 below.

Reference Example 3

To a glass-made three-necked flask (volume: 100 ml) with a condenser, 30.0 g (171 mmol) of α,α'-dichloro-o-xylene, 30.0 g of N,N-dimethylformamide and 14.2 g (86 mmol) of sodium octanoate (sodium caprylate) were added.

After the mixture was heated and stirred at 130° C. for one hour, the reaction mixture was analyzed by the gas chromatography. The conversion of α,α'-dichloro-o-xylene, the yield of [2-(chloromethyl)phenyl]methyl octanoate (based on sodium octanoate), and the molar ratio of the [2-(chloromethyl)phenyl]methyl octanoate produced to the diester compound as a by-product are shown in Table 1 below.

Reference Example 4

To a glass-made three-necked flask (volume: 500 ml) with a condenser, 133.0 g (759 mmol) of α,α'-dichloro-o-xylene, 13.3 g of N,N-dimethylformamide and 42.2 g (253 mmol) of sodium octanoate (sodium caprylate) were added. After the mixture was heated and stirred at 110° C. for 2 hours, the reaction mixture was analyzed by the gas chromatography. The conversion of α,α'-dichloro-o-xylene, the yield of [2-(chloromethyl)phenyl]methyl octanoate (based on sodium octanoate), and the molar ratio of the [2- (chloromethyl)phenyl]methyl octanoate produced to the diester compound as a by-product are shown in Table 1 below.

Reference Example 5

To a glass-made three-necked flask (volume: 100 ml) with a condenser, 8.8 g (50 mmol) of α,α'-dichloro-o-xylene, 4.0 g of N,N-dimethylformamide and 2.1 g (12.5 mmol) of sodium 2-ethylhexanoate were added. After the mixture was heated and stirred at 120° C. for one hour, the reaction mixture was analyzed by the gas chromatography. The conversion of α,α'-dichloro-o-xylene, the yield of [2-(chloromethyl)phenyl]methyl 2-ethylhexanoate (based on sodium 2-ethylhexanoate), and the molar ratio of the [2-(chloromethyl)phenyl]methyl 2-ethylhexanoate produced to the diester compound as a by-product are shown in Table 1 below.

TABLE 1

| Reference Example | Added Molar Ratio | Conversion | Yield | Produced Molar Ratio |
|---|---|---|---|---|
| Reference Example 2 | 1.0 | 83% | 49% | 68:32 |
| Reference Example 3 | 2.0 | 46% | 70% | 75:25 |
| Reference Example 4 | 3.0 | 30% | 60% | 91:9 |
| Reference Example 5 | 4.0 | 23% | 84% | 95:5 |

In Table 1, the added molar ratio means the molar amount of α,α'-dichloro-o-xylene added based on the sodium carboxylate. It is seen that the larger the added molar ratio, the smaller the amount of the diester compound produced.

Example 4

To a glass-made three-necked flask (volume: 500 ml) with a condenser, 133.0 g (0.76 mol) of α,α'-dichloro-o-xylene, 13.3 g of N,N-dimethylformamide and 63.0 g (0.38 mol) of sodium octanoate (sodium caprylate) were added.

After the mixture was heated and stirred at 120° C. for 2 hours, the reaction mixture was analyzed by the gas chromatography. As a result, the conversion of α,α'-dichloro-o-xylene was 43% and the yield of [2-(chloro-methyl)phenyl]methyl octanoate (based on sodium octanoate) was 66%. Thereafter, the reaction was distilled under reduced pressure and the distillates of N,N-dimethyl-formamide and α,α'-dichloro-o-xylene in this order were collected. The ratio in amount of the collection recovered by the distillation to the unreacted α,α'-dichloro-o-xylene was 94%. The content of [2-(chloromethyl)phenyl]methyl octanoate in 98.2 g of the distillation residue was 70.8 g (0.25 mol).

To a 1,000 ml-volume glass-made three-necked flask with a condenser, 98.2 g of the distillation residue obtained above, 15.5 g (0.32 mol) of sodium cyanide and 50.0 g of water were added. After the reaction mixture was heated and stirred at 120° C. for 2 hours, the reaction mixture was analyzed by the gas chromatography. As a result, the conversion of [2-(chloromethyl)phenyl]methyl octanoate was 93% and the yield of [2-(cyanomethyl)phenyl]methyl octanoate (based on [2-(chloromethyl)phenyl]methyl octanoate) was 67%. From the analysis by the liquid chromatography, the production of amides was verified.

To the reaction mixture obtained above, 92.0 g of a 30 wt % aqueous NaOH solution was added, and the mixed solution was heated and stirred at 110° C. for 5 hours. The resulting reaction mixture was analyzed by the gas chromatography. As a result, the conversion of [2-(cyano-methyl)phenyl]methyl octanoate was 100%.

Furthermore, to the reaction mixture, 111.0 g of concentrated hydrochloric acid (36 wt % HCl) was added, and the mixture was stirred at room temperature for 2 hours. The resulting reaction mixture was analyzed by the gas chromatography. As a result, the amount of 3-isochromanone produced in the reaction mixture was 35.8 g (0.24 mol) and the content of the octanoic acid was 40.5 g (0.28 mol). Thereafter, the reaction mixture was distilled under reduced pressure and the distillates of water, octanoic acid and 3-isochromanone in this order were collected. Then, 36.5 g of octanoic acid and 27.6 g of 3-isochromanone were collected. The content of 3-isochromanone in the distillation residue was 2.4 g. The 3-isochromanone distillate fraction was recrystallized from hexane to obtain 26.7 g (0.18 mol) of 3-isochromanone having a gas chromatography purity of 100% (area percentage). This corresponds to an actual yield of 55 mol % based on the α,α'-dichloro-o-xylene consumed.

Example 5

To a glass-made three-necked flask (volume: 500 ml) with a condenser, 133.0 g (0.76 mol) of α,α'-dichloro-o-xylene, 13.3 g of N,N-dimethylformamide and 31.1 g (0.38 mol) of sodium acetate were added. After the mixture was heated and stirred at 120° C. for 2 hours, the reaction mixture was analyzed by the gas chromatography. As a result, the conversion of α,α'-dichloro-o-xylene was 42% and the yield of [2-(chloromethyl)phenyl]methyl acetate (based on sodium acetate) was 64%. Thereafter, the reaction was distilled under reduced pressure and the distillates of N,N-dimethylformamide and α,α'-dichloro-o-xylene in this order were collected. The ratio in amount of the collection recovered by the distillation to the unreacted α,α'-dichloro-o-xylene was 96%. The content of [2-(chloromethyl)phenyl]methyl acetate in 53.7 g of the distillation residue was 43.9 g (0.22 mol).

To a 1,000 ml-volume glass-made three-necked flask with a condenser, 53.7 g of the distillation residue obtained above, 15.2 g (0.31 mol) of sodium cyanide and 50.0 g of water were added. After the reaction mixture was heated and stirred at 90° C. for 2 hours, the reaction mixture was analyzed by the gas chromatography. As a result, the conversion of [2-(chloromethyl)phenyl]methyl acetate was 97% and the yield of [2-(cyanomethyl)phenyl]methyl acetate (based on [2-(chloromethyl)phenyl]methyl acetate) was 76%. From the analysis by the liquid chromatography, the production of amides was verified.

To the reaction mixture obtained above, 63.0 g of a 30 wt % aqueous NaOH solution was added, and the mixed solution was heated and stirred at 100° C. for 3 hours. The resulting reaction mixture was analyzed by the gas chromatography. As a result, the conversion of [2-(cyano-methyl)phenyl]methyl acetate was 100%.

Furthermore, to the reaction mixture, 52.0 g of concentrated hydrochloric acid (36 wt % HCl) was added, and the mixture was stirred at room temperature for 2 hours. The resulting reaction mixture was analyzed by the gas chromatography. As a result, the amount of 3-isochromanone produced in the reaction mixture was 31.1 g (0.21 mol).

Thereafter, the reaction mixture was distilled under reduced pressure and the distillates of water, acetic acid and 3-isochromanone in this order were collected. Then, 24.9 g of 3-isochromanone were collected. The content of 3-isochromanone in the distillation residue was 3.7 g.

The 3-isochromanone distillate fraction was recrystallized from hexane to obtain 22.4 g (0.15 mol) of 3-isochromanone having a gas chromatography purity of 100% (area percentage). This corresponds to an actual yield of 47 mol % based on the α,α'-dichloro-o-xylene consumed.

[Effects of the Invention]

By the present invention, 3-isochromanones represented by formula (II) useful as a synthetic starting material of medicals or agricultural chemicals and the cyano compound represented by formula (I) can be obtained by an industrially advantageous method in a high yield.

What is claimed is:

1. A method for manufacturing a 3-isochromanone represented by the following formula (II):

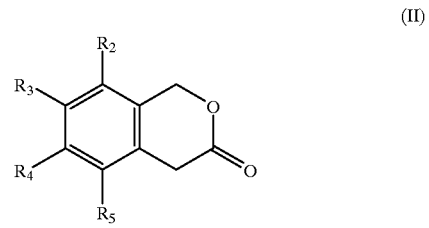

(II)

wherein $R_2$, $R_3$, $R_4$ and $R_5$ each independently represents a hydrogen atom, a halogen atom, an alkyl group or an alkoxy group, said method comprising hydrolyzing a cyano compound represented by the following formula (I):

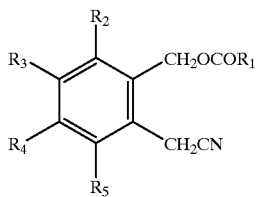

(I)

(wherein $R_1$ represents a hydrogen atom, an alkyl group or an aryl group, and $R_2$, $R_3$, $R_4$ and $R_5$ have the same meanings as defined above, and subjecting the hydrolyzate to intra-molecular cyclization.

2. The method for manufacturing a 3-isochromanone as claimed in claim 1, wherein the hydrolysis is performed in the presence of an acid or an alkali and the intramolecular cyclization is performed in the presence of an acid.

3. The method for manufacturing a 3-isochromanone as claimed in claim 2, wherein the hydrolysis is performed in the presence of an acid.

4. The method for manufacturing a 3-isochromanone as claimed in claim 1, wherein in formula (I), $R_1$ is a hydrogen atom or an alkyl group having from 1 to 9 carbon atoms.

5. The method for manufacturing a 3-isochromanone as claimed in claim 2, wherein in formula (I), $R_1$ is a hydrogen atom or an alkyl group having from 1 to 9 carbon atoms.

6. The method for manufacturing a 3-isochromanone as claimed in claim 3, wherein in formula (I), $R_1$ is a hydrogen atom or an alkyl group having from 1 to 9 carbon atoms.

7. The method for manufacturing a 3-isochromanone as claimed in claim 4, wherein in formula (I), $R_1$ is a methyl group, an ethyl group or a 3-n-heptyl group.

8. The method for manufacturing a 3-isochromanone as claimed in claim 5, wherein in formula (I), $R_1$ is a methyl group, an ethyl group or a 3-n-heptyl group.

9. The method for manufacturing a 3-isochromanone as claimed in claim 6, wherein in formula (I), $R_1$ is a methyl group, an ethyl group or a 3-n-heptyl group.

10. The method for manufacturing a 3-isochromanone as claimed in claim 1, wherein in formula (I), $R_2$, $R_3$, $R_4$ and $R_5$ each is a hydrogen atom.

11. The method for manufacturing a 3-isochromanone as claimed in claim 1, wherein the 3-isochromanone is separated by distillation from the reaction mixture of the intramolecular cyclization.

12. A method for manufacturing a cyano compound represented by formula (I) (wherein $R_1$ represents a hydrogen atom, an alkyl group or an aryl group, and $R_2$, $R_3$, $R_4$ and $R_5$ each independently represents a hydrogen atom, a halogen atom, an alkyl group or an alkoxy group), said method comprising reacting a monoester compound represented by the following formula (III):

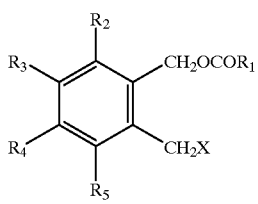

(III)

(wherein $R_1$ represents a hydrogen atom, an alkyl group or an aryl group, $R_2$, $R_3$, $R_4$ and $R_5$ each independently represents a hydrogen atom, a halogen atom, an alkyl group or an alkoxy group, and X represents a halogen atom) with a metal cyanide.

13. The method for manufacturing a 3-isochromanone as claimed in claim 1, wherein the cyano compound is manufactured by a method comprising reacting a monoester compound represented by the following formula (III):

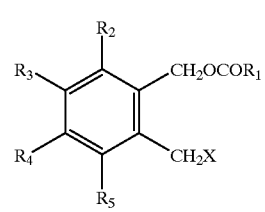

(III)

(wherein $R_1$ represents a hydrogen atom, an alkyl group or an aryl group, $R_2$, $R_3$, $R_4$ and $R_5$ each independently represents a hydrogen atom, a halogen atom, an alkyl group or an alkoxy group, and X represents a halogen atom) with a metal cyanide.

14. The method for manufacturing a 3-isochromanone as claimed in claim 4, wherein the cyano compound is manufactured by a method comprising reacting a monoester compound represented by the following formula (III):

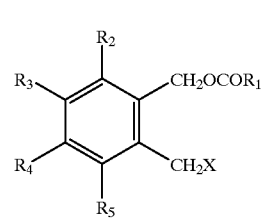

(III)

wherein $R_1$ represents a hydrogen atom, an alkyl group or an aryl group, $R_2$, $R_3$, $R_4$ and $R_5$ each independently represents a hydrogen atom, a halogen atom, an alkyl group or an alkoxy group, and X represents a halogen atom with a metal cyanide.

15. The method for manufacturing a 3-isochromanone as claimed in claim 7, wherein the cyano compound is manufactured by a method comprising reacting a monoester compound represented by the following formula (III):

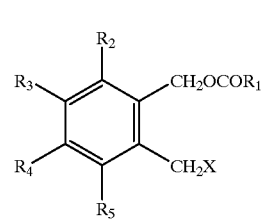

(III)

wherein $R_1$ represents a hydrogen atom, an alkyl group or an aryl group, $R_2$, $R_3$, $R_4$ and $R_5$ each independently represents a hydrogen atom, a halogen atom, an alkyl group or an alkoxy group, and X represents a halogen atom with a metal cyanide.

16. The method for manufacturing a 3-isochromanone as claimed in claim 10, wherein the cyano compound is manufactured by a method comprising reacting a monoester compound represented by the following formula (III):

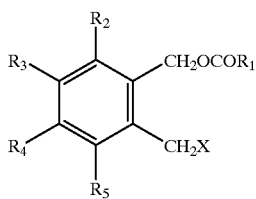

(III)

wherein $R_1$ represents a hydrogen atom, an alkyl group or an aryl group, $R_2$, $R_3$, $R_4$ and $R_5$ each independently represents a hydrogen atom, a halogen atom, an alkyl group or an alkoxy group, and X represents a halogen atom with a metal cyanide.

17. The method for manufacturing a 3-isochromanone as claimed in claim 11, wherein the cyano compound is manufactured by a method comprising reacting a monoester compound represented by the following formula (III):

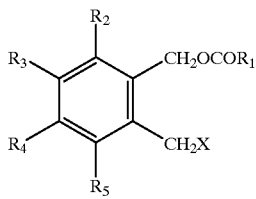

(III)

wherein $R_1$ represents a hydrogen atom, an alkyl group or an aryl group, $R_2$, $R_3$, $R_4$ and $R_5$ each independently represents a hydrogen atom, a halogen atom, an alkyl group or an alkoxy group, and X represents a halogen atom with a metal cyanide.

18. The method for manufacturing a 3-isochromanone as claimed in claim 13, wherein the monoester compound represented by formula (III) (wherein $R_1$ represents a hydrogen atom, an alkyl group or an aryl group, $R_2$, $R_3$, $R_4$ and $R_5$ each independently represents a hydrogen atom, a halogen atom, an alkyl group or an alkoxy group, and X represents a halogen atom) is manufactured by reacting an α,α'-dihalogeno-o-xylene compound represented by the following formula (IV):

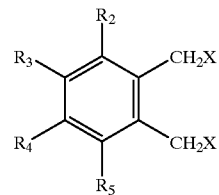

(IV)

wherein $R_2$, $R_3$, $R_4$ and $R_5$ each independently represents a hydrogen atom, a halogen atom, an alkyl group or an alkoxy group, and X represents a halogen atom with an alkali metal salt or alkaline earth metal salt of a carboxylic acid represented by $R_1COOH$ wherein $R_1$ represents a hydrogen atom, an alkyl group or an aryl group.

19. The method for manufacturing a 3-isochromanone as claimed in claim 18, wherein the α,α'-dihalogeno-o-xylene compound is reacted in an amount of 2 equivalents or more to an alkali metal salt or alkaline earth metal salt of the carboxylic acid.

20. The method for manufacturing a 3-isochromanone as claimed in claim 18, wherein after the reaction of the α,α'-dihalogeno-o-xylene compound with an alkali metal salt or alkaline earth metal salt of the carboxylic acid, the unreacted α,α'-dihalogeno-o-xylene compound is separated and recovered by distillation from the reaction mixture.

21. The method for manufacturing a 3-isochromanone as claimed in claim 20, wherein an aprotic polar solvent is added to the reaction system of the α,α'-dihalogeno-o-xylene compound with an alkali metal salt or alkaline earth metal salt of the carboxylic acid.

\* \* \* \* \*